United States Patent [19]

Leibinger et al.

[11] Patent Number: 5,201,737
[45] Date of Patent: Apr. 13, 1993

[54] PLATE FOR COVERING A DRILL HOLE IN A SKULL CAP AND FOR FIXING A CRANIAL BONE COVER

[75] Inventors: Karl Leibinger, Tuttlingen-Mohringen; Franz Leibinger, Mühlheim-Stetten, both of Fed. Rep. of Germany

[73] Assignee: Oswald Leibinger GmbH, Muhlheim, Fed. Rep. of Germany

[21] Appl. No.: 859,656

[22] Filed: Mar. 30, 1992

[30] Foreign Application Priority Data

Apr. 11, 1991 [DE] Fed. Rep. of Germany ....... 4111856

[51] Int. Cl.⁵ .............................................. A61B 17/56
[52] U.S. Cl. .......................................... 606/69; 606/70
[58] Field of Search .................. 606/69, 70, 71, 56, 606/96, 97, 98, 101, 102, 104; 411/457, 461, 469; 446/107, 126

[56] References Cited

U.S. PATENT DOCUMENTS

| 2,238,238 | 4/1941 | Westrope | 411/457 |
| 2,329,471 | 9/1943 | King | 411/461 |
| 2,791,868 | 5/1957 | Viken | 446/107 |
| 2,846,744 | 8/1958 | Becker | 411/461 |
| 4,116,200 | 9/1978 | Braun | 606/81 |
| 4,775,350 | 10/1988 | Short | 446/126 |
| 4,793,335 | 12/1988 | Frey | 411/469 |

FOREIGN PATENT DOCUMENTS

| 0290138 | 11/1988 | European Pat. Off. | 606/69 |
| 2247176 | 3/1974 | Fed. Rep. of Germany | 606/69 |

Primary Examiner—Robert Hafer
Assistant Examiner—Michael Brown
Attorney, Agent, or Firm—Brumbaugh, Graves, Donohue & Raymond

[57] ABSTRACT

A plate for covering a drill hole in a skull cap and for fixing a cranial bone cover comprises a plurality of vanes (16a-16e) extending radially with respect to a center (12) and slots (20a-20e) between the vanes. For receiving bone screws holes (18a-18e) are provided in the respective region of the outer periphery of the vanes.

17 Claims, 2 Drawing Sheets

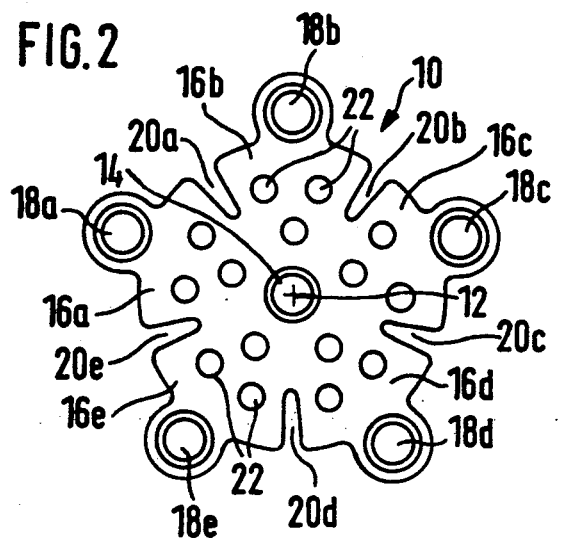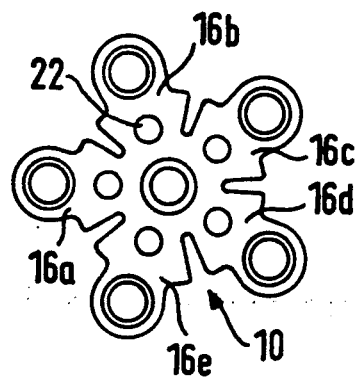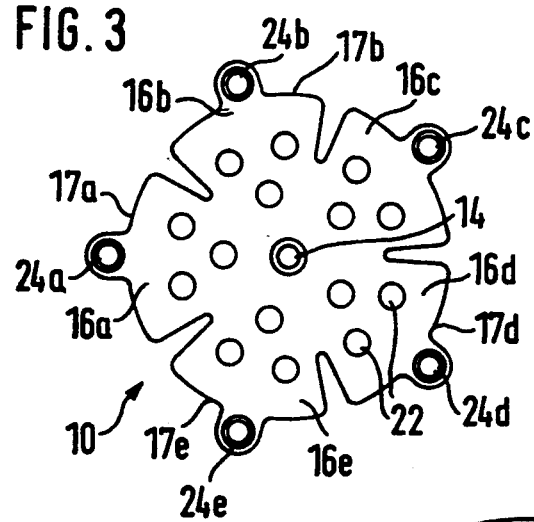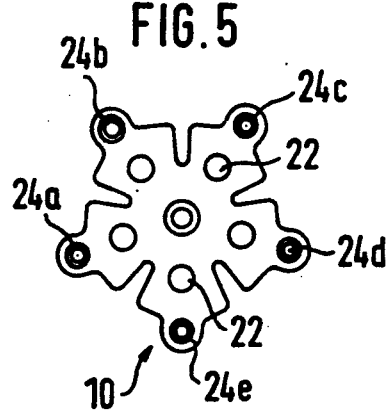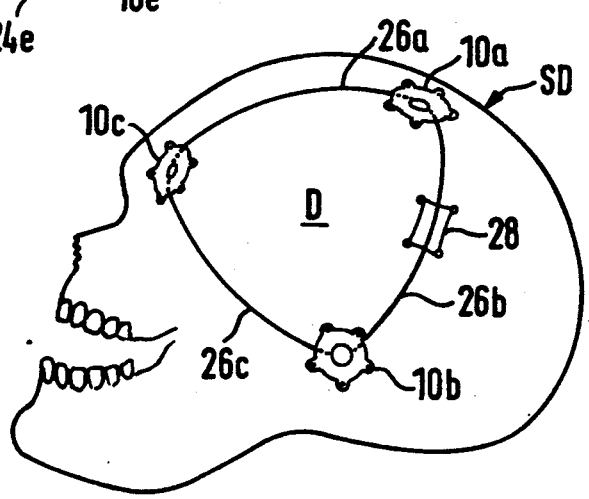

PLATE FOR COVERING A DRILL HOLE IN A SKULL CAP AND FOR FIXING A CRANIAL BONE COVER

In neurosurgical, plastic and craniofacial operations on or through the vault of the human skull, after detachment of the soft parts covering the cranial vault frequently large-area bone segments of the skull cap are detached and secured again at the same point of the skull cap or in a different position at the end of the surgical operation (refixed).

In the surgical treatment of craniofacial abnormalities, frequently one or more bone segments of the skull cap are removed and after modelling corresponding to the desired cosmetic result refixed again in a displaced position. Such operations, which are frequently carried out in infancy, serve the purpose of correcting bone malformations of the skull cap in order to permit unobstructed growth of the brain and at the same time also to improve the cosmetic appearance of the patient.

In neurosurgical operations bone covers of the skull are lifted off in various regions and sizes to permit access to the brain. As a rule, the bone segments removed in this manner (hereinafter referred to as cranial bone covers) are refixed in the original position after completion of the socalled soft part operation (i.e. the operation on the brain).

The operating technique employed in such operations frequently includes a socalled bow incision (from ear to ear over the highest point of the skull cap) through the soft parts, whereafter a subpereosteal undermining is carried out and the largest soft part lobes are folded forwardly or rearwardly.

Depending on the size, location and geometrical form of the bone cover to be lifted off, several holes are drilled through the cranial vault. If the bone cover to be removed is for example a triangular skull cap segment, as a rule three holes are drilled at the corner points of the bone cover. Thereafter, by means of a saw (which is provided with a guide nose in order to avoid dura mater injuries) the socalled connecting osteotomies are made between the drill holes; with a triangular form of the bone cover to be lifted off the connecting osteotomies are thus the sides of a spherically curved triangle. Thereafter the bone cover can be lifted off to carry out the further operation.

After completion of the operation the previously removed bone covers have to be refixed again, i.e. secured again at the desired location. Various aids are known in the prior art for this refixation of the bone cover. EP 0 290 138 A2 and EP 0 291 632 A1 describe for this purpose socalled small bone plates of body-compatible material, for example titanium or a chromium-cobalt-molybdenum alloy, which are made strip-like and at intervals are provided with holes for receiving bone screws. These elongated plates are so designed that they can be deformed by the surgeon to adapt them to the bone in the area to be treated.

EP 0 347 658 A1 described a bone plate for osteosynthesis having holes to receive bone screws and a gear mechanism between the plate parts for adjusting the relative position of the plate parts German utility models DE 85 28 003 U1 and DE 87 06 912 U1 describe bone plates employed for fixing a cranial bone cover.

The elder application published as DE 40 28 021 C1 describes an osteosynthesis grid with holes for receiving bone screws (i.e. securing screws which are screwed into the bone).

Another implant is the socalled mesh systems, in particular according to Dumbach. Here, relatively large-area perforated discs (for example of titanium) which are flexible in order to be exactly fitted by the surgeon are used as implant for bone fixation, primarily in the jaw region. The aforementioned drill holes made at the start of a trephination present particular problems. For several reasons, among others for protecting the brain covered postoperatively only by the soft parts and for improving the cosmetic result, the drill holes should also be closed after the operation. When the drill holes are made using conventional drills or trephines, as a rule however no bone plug is formed which could be refixed; on the contrary, due to the cutting action of the rotating instrument only bone meal is formed. In the prior art, the following attempts are made to solve the problem of the drill holes:

The drill holes remain unclosed. However, after the healing phase this gives a mostly unsatisfactory cosmetic result because, in particular in the region of the forehead, visible "dents" result beneath which frequently the pulsation of the brain is even visible. The covering of the drill holes simply by means of the soft parts does not provide adequate protection of the brain from injuries.

The bone meal forming when making the drill holes can be partially collected and used for covering the perforation. However, with this method adequate stability of the bone and a predictable positive cosmetic result cannot be ensured. Also, no immediate protection of the brain is obtained.

It is further known to use alloplastic materials, such as bone waxes, bone cement, etc. However, these materials do not provide reliable protection of the brain either and in addition as a rule they are exogenous implantation materials which remain in place and are not surrounded naturally in the course of time so that infections or other undesired reactions of the body can occur.

Finally, it is further known in the prior art to use plastic covers which project over the edge of the drill hole and are clamped in the drill hole itself. With this method as well no cosmetically satisfactory result is ensured (the plastic covers can project over the contour of the bone). Furthermore, due to its softness plastic does not offer reliable protection against puncture wounds. The invention is based on the problem of providing means for solving the problems explained above and permitting refixation of cranial bone covers which ensures both a reliable protection against injury and a cosmetically predictable and desired result.

This problem is solved in a plate of the type mentioned at the beginning by a plurality of vanes which extend racially with respect to a centre and which are separated from each other by slots, and of which at least some comprise at their outer peripheral portions in each case a hole for receiving a bone screw.

The plate according to the invention covers the drill hole and its outer contour is preferably substantially round, in particular circular, or polygonal. The preferably slightly concavely formed cover plate is made available in various sizes and arranged by the surgeon concentrically over the drill hole and can then be anchored securely to the cranial bone by means of bone screws.

The bone screws are led through holes in the plates according to the invention which are arranged at the outer peripheral portions of the vanes, i.e. readily adjacent (inside or outside) said portions. This optimizes the mechanical stability of the refixation.

Preferably, the holes for receiving a respective bone screw are arranged on a circle of which the centre point coincides with the centre of the plate.

Along the periphery of the plate according to the invention the holes for receiving the bone screws are preferably arranged at regular intervals, at least three holes for receiving screws being necessary and provided, in order to achieve a fixation-stable three-point anchoring. Additional holes for receiving screws increase the anchoring possibilities of the plate.

The vanes of the plate according to the invention are joined together in the interior of the plate. The entire plate is made integrally from a single material, such as titanium, niobium, etc.

The individual vanes of the plate according to the invention are separated from each other by radially extending slots. The slots extend however preferably only over a portion of the radius of the plate in order to achieve good stability in the refixation. Preferably, the slot length corresponds to approximately half the radius of the plate with an allowed deviation of $+/-30\%$, the radius being related to the solid part of the plate, i.e. without any possibly provided additional rings at the exterior of the plate for accommodating holes for receiving screws.

According to a preferred embodiment the slots between the vanes of the plate are formed conically.

The slots have inter alia two functions:

The surgeon can employ the slots as "inspection slots" and through them can see the drill hole disposed therebelow, thereby enabling the plate to be anchored centrally with respect to the drill hole in simple manner with constant lateral intervals, i.e. the substantially round or rotation-symmetrical plate can be fixed concentrically to the drill hole.

Preferably, the plates according to the invention are made available in a concave form adapted to the curvature of the skull. They can however be individually formed in accordance with the conditions of the specific use of the plate. Due to the slots between the individual vanes of the plate, the plates and in particular the vanes themselves can be adapted to almost every anatomical situation, thereby optimizing the cosmetic result obtained.

Preferably, both in the inner portion and in the vanes of the plate according to the invention holes are provided so that postoperatively blood and tissue fluid can flow out of the epidural space unrestricted.

According to another embodiment of the plate according to the invention, in the centre thereof a central screw hole is provided for the case that a possibly obtained bone plug is to be additionally screwed to the lower side of the plate.

The plate according to the invention is preferably so configured that it has as flat a profile as possible and the bone screw heads used to secure the plate are as far as possible countersunk in the plate without projection.

The plate according to the invention thus has a double function: Firstly, it serves as drill hole cover and secondly it serves for fixation of the bone cover. At least one, preferably two, screws connect the plate to the bone cover, whilst the remaining screws establish a connection over the drill hole to the rest of the cranial vault. A large number of differently dimensioned bone covers can be fixed to the skull cap in all regions of the skull by using at least two, preferably three plates. An additional stabilizing of the skull segments by the alternative fixation possibilities according to the prior art described at the beginning is not necessary but is available additionally to the surgeon if required.

Hereinafter examples of embodiment of the invention will be described in detail with the aid of the drawings, wherein:

FIGS. 2–5 show different embodiments of the plates according to the invention for covering a drill hole in a skull cap and for fixation of a cranial bone cover; and FIG. 6 shows schematically the covering of drill holes in a skull cap and the fixation of a bone cover to the skull cap using plates according to the invention.

Figure 1:
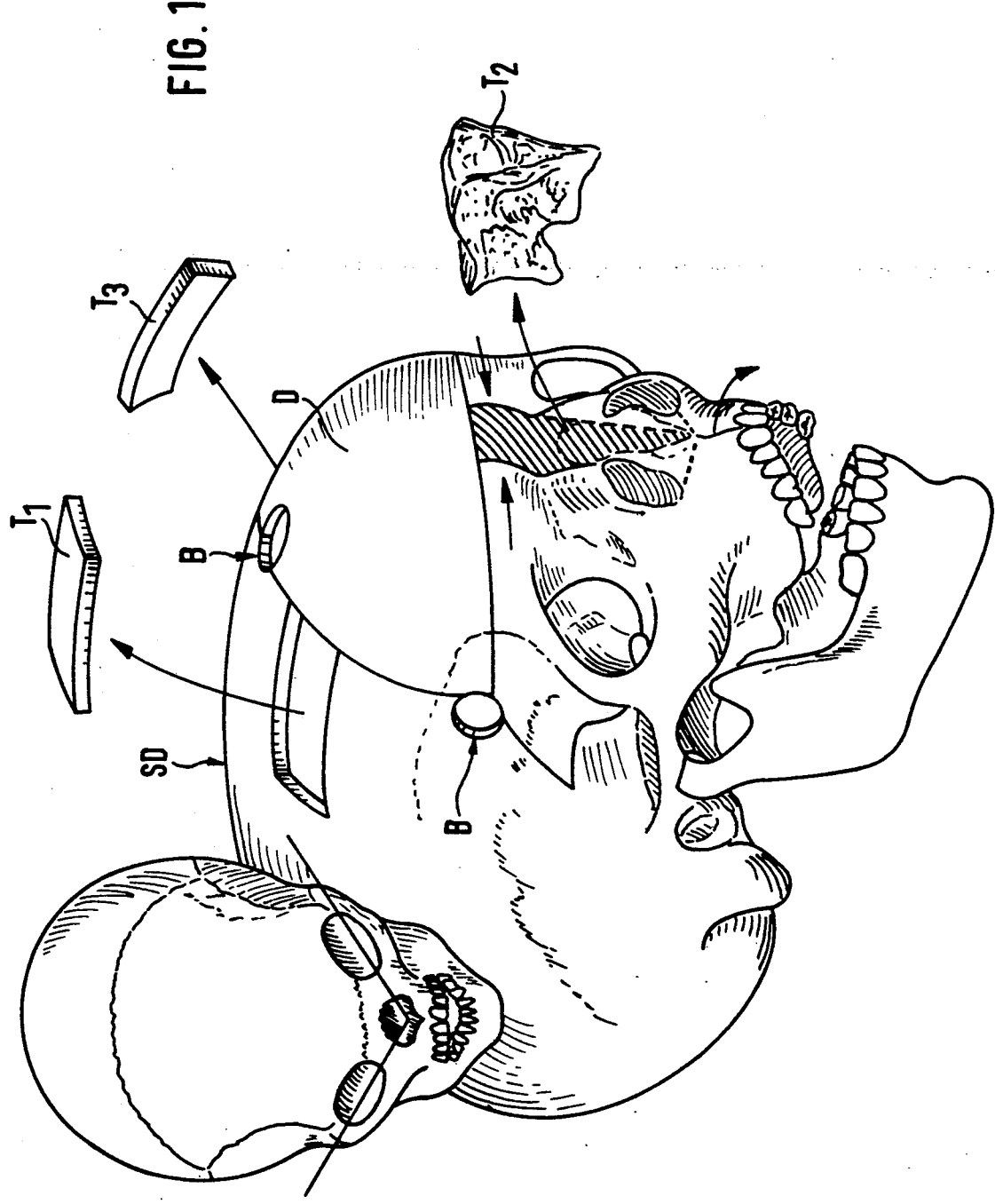
FIG. 1 shows schematically a craniofacial operation for remedying bone malformations in which a cranial bone cover and several subsegments are removed.

FIG. 1 shows schematically a skull cap SD in which bores B are formed. Between the bores B incision lines extend (cf. also FIG. 6) so that a cranial bone cover D can be removed. To remedy the osseous malformations visible in FIG. 1 portions $T_1$, $T_2$, $T_3$ of the skull are removed.

The present invention relates to refixation of the cranial bone cover D and covering of the drill holes B.

FIG. 2 shows a first example of embodiment of a plate for covering a drill hole B in a skull cap SD and for fixation of a cranial bone cover D. The plate 10 serves as implant and is made integrally from a biocompatible material, for example titanium or niobium.

FIG. 2 shows in a manner similar to FIG. 3 an example of embodiment for covering a relatively large drill hole B having diameters up to 14 mm whilst FIGS. 4 and 5 show plates which are provided for smaller drill holes having diameters up to 7 mm.

In FIGS. 2 to 5 corresponding components are provided with the same reference numerals so that only FIG. 2 need be described in detail. The examples of embodiment according to the FIGS. 3 to 5 will then be readily understandable.

The plate 10 is rotational symmetrical with respect to its centre 12. The centre 12 is disposed centrally in a hoe 14.

In the examples of embodiment illustrated the plate 10 comprises five vanes 16a, 16b, 16c, 16d and 16e.

Between the vanes 16a–16e respective slots 20a, 20b, 20c, 20d and 20e are arranged. The slots extend radially with respect to the centre 12 over about half the radius of the plate, the radius being measured from the centre 12 up to the outer peripheral portions 17a, 17b, 17c, 17d and 17e of the vanes 16a–16e, i.e. the radius does not include the radial extensions of the individual vanes in which respective holes 18a, 18b, 18c, 18d and 18e are provided for receiving bone screws. The slots are made to taper conically radially inwardly.

The entire plate 10 is provided uniformly with holes 22 so that during and after the operation blood and other fluids can flow off.

The holes 18a–18e each have countersunk portions so that the heads of bone screws (not shown) do not project.

The plate 10 including the vanes 16a–16e is made concave in such a manner that it is roughly preadapted to a skull cap SD. Due to the configuration of the plate 10 described and the slots between the vanes the operating surgeon can during the operation perform an adaptation of the shape depending upon the particular geometrical situation and bend the vanes and if necessary also the inside of the plate as desired.

The holes 18a-18e for receiving the bone screws are provided in rings 24a-24e which in the examples of embodiment illustrated project as integral projections beyond the outer peripheral portions 17a-17e of the vanes 16a-16e. The projections and the holes formed therein are in each case arranged centrally on the associated vane.

In the examples of embodiment of plates according to the invention illustrated in FIGS. 2 to 5 in each case five vanes are provided. This has been found favourable.

FIG. 6 shows the refixation of a cranial bone cover D to a skull cap SD (cf. also FIG. 1). The bone cover D has the form of a spherical triangle and the bores (not visible in FIG. 6 because they are covered by the plates) are each located at the corner points of the triangle formed by the incision lines 26a, 26b and 26c. The plates 10a, 10b and 10c according to the invention are arranged concentrically overlapping the drill holes and fix the cover D with respect to the skull cap SD. The fixation can be additionally promoted by a grid 28 known per se.

The examples of embodiment described above having five vanes can be modified in that in particular three vanes or more than five vanes are provided. An odd number of vanes if preferred. The rotational symmetry shown in the examples of embodiment illustrated (with five vanes an arc angle of 72°) facilitates handling of the plate.

The plates according to the examples of embodiment described above are essentially round (except for the attached rings 24), i.e. the main body is substantially circular about the centre 12. Modifications are possible to this preferred embodiment, in particular square or rectangular main bodies.

We claim:

1. A cranial implant for fixation to the cranial vault of a bone cover, previously removed by a procedure including drilling of at least one hole at an edge of the bone cover, and for covering the drill hole, said implant comprising:
   a plate formed of a body-compatible metal which is rotational-symmetrical with respect to a center and has a plurality of vanes which extend radially with respect to said center and are separated from each other by slots for providing visibility of at least some of the skull area beneath a plate being implanted, at least some of said vanes each having a hole at its outer peripheral portion for receiving a bone screw, with plate being adapted for centering over a drill hole during implentation whereby the holes in said vanes are so positioned relative to the drill hole that bone screws received through the holes are adapted to screw the plate to bone surrounding the drill hole and thereby fix the bone cover to the cranial vault, wherein said plate has a central hole formed therein concentric with the center of said plate, and said plate has a plurality of hole therethrough, distributed around said central hole, for allowing blood and other fluids to flow through the plate following fixation of the cranial bone cover.

2. A cranial implant according to claim 1, wherein the holes in said at least some vanes for receiving respective bone screws are arranged on a circle centered at said center of said plate.

3. A cranial implant according to claim 2, wherein each hole for receiving a respective bone screw is located centrally on the outer peripheral portion of a respective vane.

4. A cranial implant according to claim 3, wherein each of said vanes has an integral ring formed centrally on the outer peripheral portion thereof having a centrally located hole formed therein for receiving a respective bone screw.

5. A cranial implant according to claim 2, wherein each of said vanes has a ring formed at the outer peripheral portion thereof having a central located hole formed therein for receiving a respective bone screw.

6. A cranial implant according to claim 5, wherein the slots separating said vanes from each other extend radially with respect to the center of said plate over substantially the outer half of the radius of said plate.

7. A cranial implant according to claim 6, wherein said plate has a central hole formed therein concentric with the center of said plate.

8. A cranial implant according to claim 7, wherein said plate has a plurality of holes therethrough, distributed around said central hole, for allowing blood and other fluids to flow through the plate following fixation of the cranial bone cover.

9. A cranial implant according to claim 1, wherein each of said vanes has a ring formed at the outer peripheral portion thereof having a hole formed therein for receiving a respective bone screw.

10. A cranial implant according to claim 1, wherein the slots separating said vanes from each other extend radially with respect to the center of said plate.

11. A cranial implant according to claim 10, wherein the slots separating said vanes extend radially over substantially the outer half of the radius of said plate.

12. A cranial implant according to claim 11, wherein said slots are conical tapered radially inwardly, being widest at their outer extremity.

13. A cranial implant according to claim 11, wherein said slots are conically tapered radially inwardly, being widest at their outer extremity.

14. A cranial implant according to claim 1, wherein said plate has an odd number of vanes.

15. A cranial implant according to claim 1, wherein said plate has five vanes rotational-symmetrical with respect to the center of said plate.

16. A cranial implant according to claim 1, wherein said plate is normally flat but is permanently deformable to the contour of the skull.

17. A cranial implant according to claim 1, wherein said plate is shaped during manufacture to have a concavely curved bottom surface.

* * * * *